Figure 1:
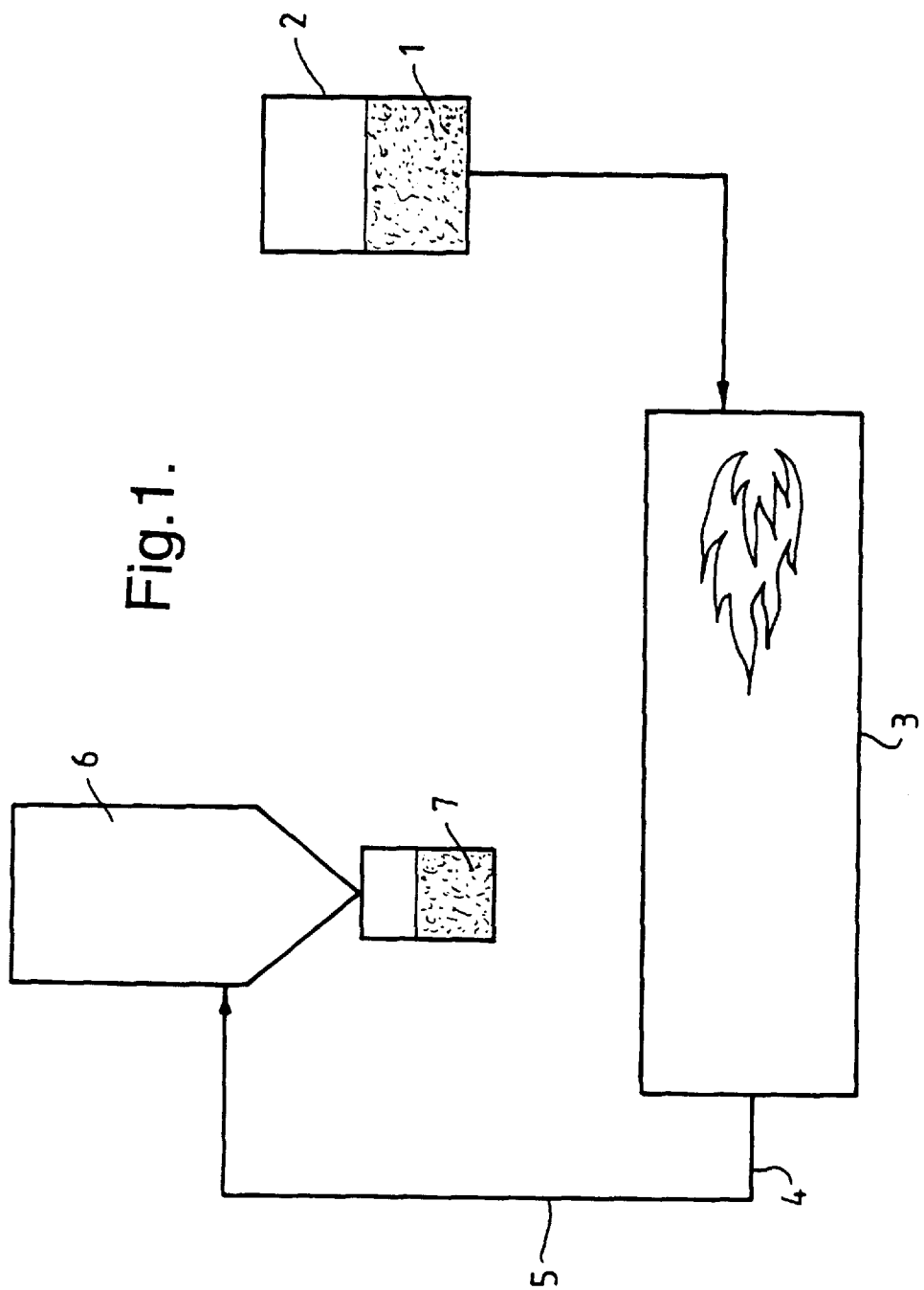

United States Patent [19]
Laundon

[11] Patent Number: 5,876,688
[45] Date of Patent: *Mar. 2, 1999

[54] ZINC OXIDE AND A PROCESS OF MAKING IT

[75] Inventor: Roy David Laundon, Cleveland, United Kingdom

[73] Assignee: Elementis UK Limited, London, England

[ * ] Notice: This patent issued on a continued prosecution application filed under 37 CFR 1.53(d), and is subject to the twenty year patent term provisions of 35 U.S.C. 154(a)(2).

[21] Appl. No.: 586,717

[22] PCT Filed: Jul. 27, 1994

[86] PCT No.: PCT/GB94/01613

§ 371 Date: Mar. 6, 1996

§ 102(e) Date: Mar. 6, 1996

[87] PCT Pub. No.: WO95/04704

PCT Pub. Date: Feb. 16, 1995

[30] Foreign Application Priority Data

Aug. 6, 1993 [GB] United Kingdom .................... 9316437

[51] Int. Cl.⁶ ..................................................... C01G 9/02
[52] U.S. Cl. .......................... 423/622; 423/623; 106/425; 106/429
[58] Field of Search ..................... 106/425, 429; 423/622, 623

[56] References Cited

U.S. PATENT DOCUMENTS

| | | | |
|---|---|---|---|
| 2,747,966 | 5/1956 | Calbeck | 106/425 |
| 4,292,290 | 9/1981 | Tunison, III | 423/622 |
| 4,410,446 | 10/1983 | Cheng et al. | 252/309 |
| 4,574,063 | 3/1986 | Scherer | 264/60 |
| 4,595,574 | 6/1986 | Matsuoka et al. | 423/622 |
| 5,338,353 | 8/1994 | Uchino et al. | 106/429 |
| 5,391,354 | 2/1995 | Petersen et al. | 423/622 |

FOREIGN PATENT DOCUMENTS

| | | |
|---|---|---|
| 0 129 625 A1 | 1/1985 | European Pat. Off. . |
| A 3-7201 | 1/1991 | Japan . |
| A-3-200878 | 9/1991 | Japan . |
| 2 264 487 | 9/1993 | United Kingdom . |
| WO 90/14307 | 11/1990 | WIPO . |

OTHER PUBLICATIONS

*Chemical Abstracts*, vol. 117 (1992), Abstract No. 117: 10894t, "Preparation of zinc oxide fine particles by ultrasonic spray pyrolysis and the microstructure of the particles", p. 172.

Liu et al., "Preparation of spherical fine ZnO particles by the spray pyrolysis method using ultrasonic atomization techniques", *Journal of Materials Science 21*, (1986), pp. 3698–3702.

S. Tichy, *SOFW–Journal 119*, Jahrgang, Aug. 1993, "ZnO for Sun Protection: Transparent ZNO for Skin– and Sun-protection", (1993).

Sakai Chemical Industry Co., Ltd., Technical Data No. 1, "Finex–25, 50".

*Chemical Abstracts*, vol. 117 (1992), Abstract No. 117: 133897d.

(List continued on next page.)

*Primary Examiner*—Melissa Bonner
*Attorney, Agent, or Firm*—Oliff & Berridge, PLC

[57] ABSTRACT

A process for preparing zinc oxide comprises introducing, into an atmosphere, an aqueous solution of a zinc salt that is thermally decomposable to zinc oxide, the atmosphere having a temperature sufficient to decompose the salt to the oxide, and recovering zinc oxide. The zinc oxide so-prepared is in the form of discrete particles which can have an average particle size of 0.08 μm or less in diameter and a surface area of at least 12.5 m²/g and which is also free of zinc metal. The small particle size zinc oxide is particularly useful as a UV absorbing/scattering additive.

14 Claims, 1 Drawing Sheet

OTHER PUBLICATIONS

M. Andres–Verges et al., "Spherical and rod–like zinc oxide microcrystals: morphological characterization and microstructural evolution with temperature," *Journal of Materials Science*, vol. 27, No. 14, 1992, pp. 3756–3762.

M.L. Nielsen et al., *Ultrafine Particles*, "Ultrafine Metal Oxides by Decomposition of Salts in a Flame", The Electrochemical Society, Inc., New York, New York, 1963, pp. 181–195. No month.

"Make Metal and Ceramic Powders Continuously," *High–Tech Materials Alert*, 9(1992)Jul., No. 7, Englewood, New Jersey, p. 3.

Xiaming et al, "Preparation of Ultrafine ZnO Powders by Spray–ICP", Ceramic Powder Sci. IV, pp. 153–156, 1991.

Tichy, "Transparent ZnO for Skin– and Sunprotection", SOFW Jour., 119, Aug. 1993.

Finex–25 Technical Data, No date.

Andres–Verges et al, "Spherical and Rod–like Zinc Oxide Microcrystals: Morphological Characterization and Microstructural Evolution With Temperature", Jour. mater. Sci. 27 (14), pp. 3756–3762, 1992 no month.

ZINC OXIDE AND A PROCESS OF MAKING IT

FIELD OF THE INVENTION

This invention relates to zinc oxide having a small particle size and a process for making it.

BACKGROUND OF THE INVENTION

The ability of zinc oxide to absorb ultra-violet radiation is well known. However, zinc oxide produced by standard methods is a white, opaque powder and as such is unacceptable in appearance for use in certain applications where effective absorption of ultra-violet radiation is desirable, e.g. sunscreens, paints, varnishes, plastics, cosmetics etc.

In theory, reducing the particle size of zinc oxide to below the wavelength of visible light will result in visible light being transmitted through the zinc oxide thereby causing it to appear virtually transparent when in a dispersed form e.g. a dispersion in oil. At the same time however, such a small particle size will more effectively scatter and absorb ultra-violet light.

Methods have been developed in an attempt to provide zinc oxide having a reduced particle size so as to render it transparent when in a dispersed form.

The so-called French process comprises oxidation of zinc metal vapour by mixing with air and quenching with excess air. The particle size of the resulting zinc oxide can be decreased by increasing the rate of mixing and quenching. However, the process inevitably produces a proportion of unreacted zinc metal in the zinc oxide product, and the smaller the particle size of the oxide product the higher the level of zinc metal impurity.

Zinc metal is an extremely undesirable impurity, particularly when the zinc oxide contaminated with it is to be used in products such as sunscreens, paints, plastics etc., because it is capable of reaction with air, moisture and organic media to generate undesirable gaseous products. In addition, it tends to impart a grey tinge to the product which is aesthetically undesirable, and is often coarser than the zinc oxide thereby tending to impart a gritty feel to the product.

An article by S. Tichy, SOFW—Journal 119. Jahrgang, August 1993, discloses "micronized" zinc oxide produced by first precipitating the basic carbonate from a purified solution of zinc sulphate or zinc chloride, washing and filtering the carbonate, and finally subjecting it to calcination. The process involves a number of separate steps each of which tends to give rise to a loss in yield of the final product.

The "micronized" zinc oxide is transparent and allegedly has a particle size of about 20 nm and a surface area in the range 50 to 150 $m^2/g$. However, scanning electron micrograph studies of the "micronized" zinc oxide have shown it to have a particle size of around 1 $\mu$m and to have a sponge-like, or internally porous, structure which accounts for the high surface area.

In addition, when zinc chloride is used in the process, the zinc oxide product tends to be contaminated with chloride which is undesirable, particularly in cosmetics applications, for example, where purity of ingredients is essential.

Another process for making small zinc oxide is disclosed in an article by Liu et al., Journal of Materials Science 21 (1986) 3698–3702. This process comprises dissolving zinc acetate dihydrate in methanol, atomising this solution into very fine (around 2 $\mu$m) droplets using an ultrasonic atomiser, and passing these first into a low temperature electric furnace and subsequently into a high temperature electric furnace. One disadvantage with this process is in the use of methanol as a solvent, since this is both expensive, particularly in the high volumes used compared to a relatively small amount of zinc acetate, and dangerous due to its high flammability. Another disadvantage resides in the use of ultrasonic atomisation since this is both difficult and expensive to apply to a large sale.

The zinc oxide produced comprises slightly porous, spherical particles having a mean diameter of 0.15 $\mu$m and having a surface area of about 50 $m^2/g$. Each particle consists of an agglomerate of a number of smaller individual, or "primary", particles each having a diameter in the range 100 to 200 nm. The relatively high surface area quoted is that of the agglomerate and includes the exposed surface area of each of the "primary" particles.

It would be desirable to produce zinc oxide having a small particle size and that is free of zinc metal impurity by a process that is simple, safe and economical when applied to a large, or production, scale.

SUMMARY OF THE INVENTION

According to one aspect of the present invention, a process for preparing zinc oxide comprises the steps of:

introducing, into an atmosphere, an atomised aqueous solution of a zinc salt that is thermally decomposable to zinc oxide, the atmosphere having a temperature sufficient to decompose the salt to the oxide, and recovering zinc oxide.

This process is simple and cost-effective. In addition, the selection of certain process conditions, described below, allow accurate control of the particle size of the resulting zinc oxide.

According to a further aspect of the invention zinc oxide is obtainable by the above described process.

According to yet a further aspect of the invention zinc oxide in the form of discrete particles all of which have an average particle size of 0.08 $\mu$m or less in diameter and a surface area of at least 12.5 $m^2/g$ and which is free of zinc metal.

By virtue of its discrete small particles the zinc oxide of the invention is very effective in absorbing ultra-violet radiation. In addition, the absence of zinc metal impurity from the oxide means that the undesirable effects normally associated with that impurity, which are described above, are not experienced.

DESCRIPTION OF THE INVENTION

It is convenient to consider the process of the invention first. The water-soluble zinc salt that is decomposed to the oxide may be selected from soluble organic salts such as the acetate, formate and other carboxylates, or from the nitrate, chloride and sulphate. The preferred salts are the acetate and the formate on account of their good solubility and relatively low temperature of decomposition; in each case the salt is usually the dihydrate. The formate may be preferred in some cases for cost reasons because it requires less oxygen to thermally decompose it to the oxide.

The salt is formed into an aqueous solution prior to atomisation. The concentration of the solution can be the room temperature solubility of the salt. However, studies of the process have indicated that the particle size of the zinc oxide produced is dependent to an extent on the concentration of the aqueous salt solution used. A higher concentration tends to give a smaller particle size, which may be preferred.

For example, the concentration can be at least 20% by weight, preferably at least 30% by weight, and more preferably at least 50% by weight. Concentration can be increased further, for example to 60% by weight or above, provided that does not hinder atomisation. These higher concentrations are obtained by preparing hot solutions.

The use of more highly concentrated solutions may also be preferred on economic grounds, since less water will be present to be evaporated from the salt thereby saving on energy fuel required to do this. In addition, smaller bag filters may be used, again representing a saving on costs.

Atomisation can be carried out by any suitable means which gives a spray comprising droplets of the aqueous salt solution of the required size. For example, it can be carried out using a "two fluid", pressure or ultrasonic atomiser. Studies have indicated that the droplet size of the atomised spray tends to affect the particle size of the zinc oxide produced. Preferably the droplet size is in the range 1 to 500 $\mu$m, and more preferably is in the range 100 to 200 $\mu$m.

It may be thought surprising that the fine particle sizes of the invention are achieved from relatively large spray droplets. Without wishing to be bound by theory, one explanation of the formation of particles from the preferred spray droplet size is that initial evaporation of the droplet when it meets the flame occurs to give a sphere of zinc acetate filled with solution. This fluid however is heated so it expands, violently shattering the zinc acetate crust giving very small fragments of zinc acetate which decompose further to give ZnO. These fragments eventually give smooth rounded particles which are collected. With larger droplets, found with higher aspiration rates for example, the shell of solid acetate will be thicker due to slower evaporation and hence the particles finally produced will be larger than is preferred. Conversely, small droplets, associated with low aspiration rates for example, will evaporate very quickly giving solid spheres which will also give rise to particles of zinc oxide larger than is preferred.

The atmosphere, into which the atomised spray is introduced, is typically a flame or a plasma, preferably a flame on economic grounds, which is typically housed, or produced, in a combustion chamber. The temperature of the atmosphere is above that of the decomposition temperature of the zinc salt. Suitable temperatures are in the range 250° C. to 2000° C., and are typically well in excess of 1000° C. These higher temperatures tend to cause rapid evaporation of water from the droplet. If an oxidising atmosphere is used this has the advantage that waste products are converted into easily disposable form, eg. $CO_2$ and water vapour.

Typically the residence time in the oxidising atmosphere is in the range 0.5 to 10 seconds, preferably 1 to 3 seconds.

The zinc oxide formed in the decomposition is injected with air, referred to in the following as secondary air, as it exits from the oxidising atmosphere, and typically from the combustion chamber. It tends to be the temperature at this stage, referred to in the following as the exit temperature, in the process that affects the ultimate particle size of the zinc oxide product, particle size being proportional to the exit temperature used. The exit temperature is typically controlled by varying the volume of secondary air and the temperature of the oxidising atmosphere.

Preferred exit temperatures are in the range 400° to 850° C., more preferably 500° to 650° C. However the preferred temperatures may vary depending upon the salt, drop size etc.

The zinc oxide is carried out of the combustion chamber in an air stream and is cooled to enable it to be collected, typically in a bag filter. Depending on the material of the bag filter, the zinc oxide may be cooled to 100° C. to 350° C. by the injection of dilution air and/or the application of an atomised water spray.

The process of the invention allows highly accurate, reproducible control of the particle size of zinc oxide through variation, in particular, of the exit temperature and the solution concentration, as described above.

The zinc oxide so produced typically comprises a white, free-flowing powder of fine particle size, and is free of zinc metal impurity. The particles are discrete particles in that they do not show the usual adherent characteristics of prior art zinc oxides tending to cause agglomeration, i.e. they are separate, and remain separate, from one another.

Zinc oxide particles can be produced that have an average particle size of around 0.1 $\mu$m or less in diameter. Preferably, however, substantially all the particles have an average particle size of 0.08 $\mu$m or less in diameter and a surface area of at least 12.5 $m^2/g$, and more preferably they have an average particle size of 0.05 $\mu$m or less in diameter and a surface area of at least 20 $m^2/g$. Particles can be produced by this process having surface areas up to 70 $m^2/g$. However, a consequence of increased surface area is that increased energy is required to disperse or emulsify the particles. This may mean that very high surface areas are undesirable for some applications.

It is preferred that the distribution of particle size within the product of the invention is relatively small. A product having a small distribution of particle sizes as described above is a very effective UV radiation absorber.

It is preferred that the particles are substantially non-porous, by which we mean that they are of substantially uniform density and have substantially no internal structure, e.g. pores, giving rise to extra, internal, surface area.

The zinc oxide prepared by the process of the invention can be used in general as a UV radiation absorbing/scattering additive.

According to yet a further aspect of the invention, a dispersion or an emulsion comprises up to 50% by weight, preferably up to 20% by weight, of zinc oxide prepared as described above or as described above.

If it is an emulsion it may be a water-in-oil or an oil-in-water emulsion.

The dispersion or emulsion can be a coating formulation, e.g. a suncare product, a paint, a varnish, a cosmetic product, or a polish. Alternatively it can be a film or moulded structure, for example of plastics material.

The fine particle size of the zinc oxide of the invention causes it to have enhanced chemical reactivity, or example as a catalyst in the rubber, or other, industry or as a fungicide.

The process of the invention is illustrated by reference to the flow chart shown in the accompanying drawing, FIG. 1.

Referring to FIG. 1, the solution (1) is held in a tank (2) and, is transferred to a combustion unit (3) housing a flame. After passing through the combustion unit the oxidised products and flue gases are cooled by dilution air (4) and by atomised water spray (5) before passing through a bag filter (6) and being collected as final product (7).

The process of the invention is further illustrated by reference to the following example.

EXAMPLE

A 200 liter solution of zinc acetate dihydrate is prepared by diluting glacial acetic acid (36 kg) to 200 liters and adding 26 kg of ZnO (stoichiometric excess) over 2 hours. The reaction mixture is stirred for a further 3 hours, excess ZnO is removed by filtration through a filter press.

The resulting clear solution was analysed and contained 32.6% (w/v) Zn $(OAc)_2 2H_2O$.

The solution is fed into a combustion chamber which is a horizontal refractory-lined steel—cylindrical shell of internal diameter 0.75 m and length 4 m. At one end of this combustion chamber is located an oil or gas burner. An atomised spray of the salt solution is produced by a two fluid atomiser, and is injected into the flame of the burner. The residence time is approximately 2 seconds. Secondary air is injected to provide exit temperatures of 500° C., 650° C., 750° C., 850° C. A 50% diluted zinc acetate solution is also used at an exit temperature of 650° C.

After passing through the combustion unit the oxidised product and exhaust gases are cooled by dilution air and by atomised water spray. The product is then collected in a bag filter.

Without wishing to be bound by theory, water is lost from zinc acetate dihydrate during the decomposition at about 100° C., and then the zinc acetate decomposes to zinc oxide and acetic anhydride, the latter in turn burning to give carbon dioxide and water.

Table 1 summarises the operating conditions and results obtained.

TABLE 1

| | | RUN NUMBER | | | | |
|---|---|---|---|---|---|---|
| | Units | 1 | 2 | 3 | 4 | 5 |
| Exit Temp. | °C. | 500 | 650 | 750 | 850 | 650 |
| $Zn(OAc)_2 2H_2O$ conc. | % w/v | 32.6 | 32.6 | 32.6 | 32.6 | 16.3 |
| Surface Area | $m^2/g$ | 35.6 | 22.3 | 16.4 | 12.5 | 16.8 |
| ZnO Assay | % | 98.4 | 99.9 | 99.5 | 99.9 | 99.5 |
| Bulk Density | g/ml | 0.09 | 0.095 | 0.084 | 0.106 | 0.112 |

(1) It is apparent from these results that:

(1) The zinc acetate was fully decomposed in the combustion unit over the range of exit temperatures examined (500°–850° C.) and the residence time used (approximately 2 seconds).

(2) Surface area decreased approximately linearly with temperature. The range of surface areas obtained was 12.5 $m^2/g$ to 35.6 $m^2/g$.

(3) Dilution (by 50% with water) gave a lower surface area product.

(4) Bulk densities of the powdered zinc oxide were very low, typically about 0.1 g/ml.

I claim:

1. A process for preparing zinc oxide comprising the steps of:

introducing, into an oxidizing flame or plasma having a temperature of from 250° C. to 2,000° C., an atomised aqueous solution of an organic zinc salt that is thermally decomposable to zinc oxide; and recovering zinc oxide.

2. A process according to claim 1, wherein the salt is selected from zinc acetate and zinc formate.

3. A process according to claim 1, wherein the concentration of the salt in the aqueous solution is at least 30% by weight.

4. A process according to claim 3, wherein the concentration of the salt in the aqueous solution is at least 50% by weight.

5. A process according to claim 1, wherein the atomised salt solution has a droplet size of 1 to 500 $\mu m$.

6. A process according to claim 1, wherein the zinc oxide exits from the oxidizing flame or plasma at a temperature in the range of 400° to 850° C.

7. The process of claim 1, wherein the atomised aqueous solution of an organic zinc salt is introduced into an oxidising flame.

8. In a process for forming a molded structure comprising the steps of forming zinc oxide, mixing the zinc oxide with a plastic material, and shaping the mixture to form a molded structure, the improvement comprising forming the zinc oxide by:

introducing, into an oxidizing flame or plasma having a temperature of from 250° C. to 2,000° C., an atomised aqueous solution of an organic zinc salt that is thermally decomposable to zinc oxide; and recovering zinc oxide.

9. The process of claim 8, wherein the atomised aqueous solution of an organic zinc salt is introduced into an oxidising flame.

10. In a process for forming a dispersion comprising the steps of forming zinc oxide and dispersing the zinc oxide in a liquid, the improvement comprising forming the zinc oxide by:

introducing, into an oxidizing flame or plasma having a temperature of from 250° C. to 2,000° C., an atomised aqueous solution of an organic zinc salt that is thermally decomposable to zinc oxide; and recovering zinc oxide.

11. The process of claim 10, wherein the atomised aqueous solution of an organic zinc salt is introduced into an oxidising flame.

12. In a process for forming an emulsion comprising the steps of forming zinc oxide and emulsifying the zinc oxide in a liquid, the improvement comprising forming the zinc oxide by:

introducing, into an oxidizing flame or plasma having a temperature of from 250° C. to 2,000° C., an atomised aqueous solution of an organic zinc salt that is thermally decomposable to zinc oxide; and recovering zinc oxide.

13. The process of claim 12, wherein the atomised aqueous solution of an organic zinc salt is introduced into an oxidising flame.

14. In a process for forming a film comprising the steps of forming zinc oxide, mixing the zinc oxide with a plastic material, and casting the mixture as a film, the improvement comprising forming the zinc oxide by:

introducing, into an oxidizing flame or plasma having a temperature of from 250° C. to 2,000° C., an atomised aqueous solution of an organic zinc salt that is thermally decomposable to zinc oxide; and recovering zinc oxide.

* * * * *